United States Patent
Hendricks et al.

(10) Patent No.: US 6,528,277 B1
(45) Date of Patent: *Mar. 4, 2003

(54) INDICATOR SYSTEMS FOR DETERMINATION OF STERILIZATION

(75) Inventors: Judy K. Hendricks, Albuquerque, NM (US); Shaundrea L. Rechsteiner, Lambertville, MI (US); Joel R. Gorski, Marrietta, GA (US); Adam Lee, Toledo, OH (US); Roger Fiske, Findlay, OH (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/698,573

(22) Filed: Oct. 27, 2000

Related U.S. Application Data (63) Continuation-in-part of application No. 09/444,830, filed on Nov. 22, 1999, now abandoned.

(51) Int. Cl.⁷ .............................. C12Q 1/22; C12Q 1/54; C12Q 1/32; C12M 1/34
(52) U.S. Cl. .............................. 435/31; 435/14; 435/26; 435/29; 435/287.4; 435/287.1; 435/283.1; 435/807; 435/810; 422/50
(58) Field of Search .............................. 435/31, 14, 26, 435/29, 287.4, 287.1, 283.1, 807, 810; 422/50

(56) References Cited

U.S. PATENT DOCUMENTS 5,830,683 A * 11/1998 Hendricks et al. ............ 435/31
5,989,852 A * 11/1999 Hendricks et al. ............ 435/31

* cited by examiner

Primary Examiner—Louise N. Leary
(74) Attorney, Agent, or Firm—John A. Burtis (57) ABSTRACT

This invention relates to a container and method for detecting a specific environmental parameter or combination of parameters, or for determining the effectiveness of a sterilization procedure. The invention relates to test indicators containing controlled volumes of compressed, gas-permeable materials, and modified caps comprising one or more apertures, sterilant permeable inserts, protruding members, or a combination thereof, and to methods for using test indicators for determining the efficacy of different types of sterilization processes. If proper sterilization conditions are not met, the interactive enzyme system remains active, and a color product forms upon the addition of the remaining components of the enzyme system. If the proper sterilization conditions are met, the sterilant destroys the interactive enzymes and no color product is formed. Inactivation of the enzyme system parallels the inactivation of bacterial spores subjected to the sterilization process. Results are available in from a few seconds to a few hours. The test indicator can also be placed into a container with material such that the design simulates an environmental parameter test of the sterilization process.

31 Claims, 5 Drawing Sheets

INDICATOR SYSTEMS FOR DETERMINATION OF STERILIZATION

RELATED APPLICATION

This application is a continuation-in-part of U.S. patent application Ser. No. 09/444,830 filed Nov. 22, 1999, now abandoned.

INTRODUCTION

This invention relates to indicator systems comprising a container containing an environmental sensing system and cap system separating the sensing system from its surroundings. Indicator systems can be used for the determination of sterilization in a variety of sterilizations processes or in determining the efficacy of an environmental test such as a test for air removal from a sterilization chamber.

BACKGROUND OF THE INVENTION

In health care, as well as many other industries, it is nearly always necessary to monitor the effectiveness of processes used to sterilize equipment such as medical devices, instruments and other disposable or nondisposable articles, and often waste. In these settings, sterilization is generally defined as the process of completely destroying all viable microorganisms including structures such as viruses, spores, yeasts and fungus. Standard practice in hospitals is to include a sterility indicator in a batch of articles to be sterilized. The use of sterility indicators allows a direct and sensitive approach to assay the lethality of the sterilization process.

A standard type of biological sterility indicator includes a known quantity of test microbial spores. This indicator is placed into the sterilization chamber and exposed to the sterilization process along with the objects to be sterilized. The test microorganisms, for example *Bacillus stearothermophilus* or *B. subtilis* spores, are incubated for a specified period of time under conditions which favor proliferation and examined for possible growth, such as turbidity in the growth medium or the presence or absence of certain metabolic products of any surviving microorganisms. Positive growth, indicating the presence of a viable spore, indicates that the sterilization process was insufficient to destroy all of the microorganisms. While the apparatus for containing the spores has varied continuously, the general sterility detection process has not. Many such indicators are disclosed in U.S. Pat. Nos. 3,239,429; 3,440,144; 4,596,773; 4,717,661; 4,732,850 and 5,167,923.

The largest use of sterility indicators occurs in research and the health care industry. Typically, such facilities have limited resources and must reuse their materials and instruments within 24 to 48 hours after sterilization and often immediately. Conventional sterility indicators normally require that the microorganisms be cultured for at least two and often up to seven days to assure adequate detection of any surviving microorganisms. During this time, items which go through the sterilization process, should not be used until the results of the spore viability test have been determined. Consequently, a holding period for sterility verification is often required. This holding period is both impractical and inefficient and, thus, the major drawback of all conventional sterility indicators.

The use of an enzyme and its subsequent activity as an indicator in detecting sterility has been described in U.S. Pat. No. 5,073,488. This technology has been greatly advanced with U.S. Pat. No. 5,486,459 which describes the use of a plurality of interactive enzymes. This technique involves subjecting a set of interactive enzymes to a sterilization cycle. Following completion of the cycle, the set is incubated with a substrate which is acted upon by the enzymes and transformed into a detectable product. Enzyme-modified product can be detected, for example, colorimetrically or fluorometrically. This method has been proven to be accurate and detection speeds are greatly accelerated as compared to spore systems. In fact, definitive results using interactive enzyme technology can be determined in less than a few minutes.

Sterility indicators are often placed in special packaging or wraps to simulate the condition of wrapped goods being processed in a sterilizer. If the articles to be sterilized are in special wrappings or packaging, the sterilant needs to effectively pass through the wrappings to destroy microorganisms on the article. To test the effectiveness of the sterilant passing through additional materials, sterility indicators are placed in challenge packs. These packs impede the sterilant as would the wrappings and thereby represent the conditions of wrapped goods in a sterilizer.

There are international standards such as the International Organization for Standardization (ISO) and the European Standards (EN) that deal with sterilization testing including steam sterilization. International standards dealing with biological indicators and testing procedures are found in the ISO 11138 series and EN 860 series. International standards for the air removal tests for pre-vacuum steam sterilizers comprises a chemical indicator in a test pack are found in the ISO 11140 series and EN 867 series. These packs incorporate the Bowie-Dick test and have similar performance standards as seen in AAMI (American Association of Medical Instrumentation), but use different testing procedures.

AAMI has proposed guidelines for challenge packs containing indicators that are assembled by hospital workers to simulate the conditions of wrapped goods in a steam or ethylene oxide sterilizer. Materials required for an AAMI challenge pack for a steam sterilizer include sixteen freshly laundered huck towels, autoclave tape and sterility indicators. In one method, each towel is folded length-wise into thirds and then folded width-wise in half. Towels are placed one on top of another with the folds opposite each other. Sterility indicators are placed between the eighth and ninth towels and the pack is secured with autoclave tape. The AAMI steam challenge pack is placed into a steam autoclave for the appropriate amount of time. Upon completion of a cycle, the indicators are processed to determine if the sterilization process was sufficient to inactivate the indicators buried in the pack.

In the case of ethylene oxide sterilization, AAMI recommends placing a sterility indicator into a plastic syringe so that the plunger is not touching the indicator. In this case, the needle end of the syringe is open. Two such syringes are placed in the center of a stack of folded towels and the stack is wrapped in a single towel. For routine monitoring, the syringe and indicator can be wrapped in a single towel and placed into a peel pouch.

Tests are also performed that evaluate the effectiveness of air removal in a prevacuum steam sterilizer. Prevacuum steam sterilizers are used to minimize the amount of air present in the sterilization chamber, thus enhancing the penetration of steam into porous loads. A prevacuum sterilizer air removal test is also known as the Bowie-Dick test or a prevacuum sterilizer residual air test.

AAMI guidelines for the Bowie-Dick test pack state that the standard pack is made using folded cotton surgical towels. Several towels are folded to create a stack 10 to 11 inches high with a rectangular border of 9 by 12 inches. A Bowie-Dick test sheet, which comprises a pattern of chemical indicator ink or indicator type on a porous sheet, is placed in the center of the pack. The pack is wrapped in a single cotton wrap and processed in a steam prevacuum sterilizer. The acceptance criterion is that the test sheet or tape darkens uniformly after processing. In other words, the chemical indicator ink changes color upon exposure to steam and if the entire sheet shows a uniform color change, there was no residual air to impede the steam.

AAMI guidelines state that other devices may be used in place of the AAMI challenge packs and Bowie-Dick tests if they provide equivalent results to the AAMI packs. Enclosure of sterilization indicators in various fibrous materials, analogous to textiles such as the towels used in the AAMI challenge packs, has been proposed in U.S. Pat. Nos. 5,200,147; 5,252,484 and 5,223,401. Packages in which a sterilization indicator is surrounded by porous material to replace some of the towels are described in U.S. Pat. No. 4,692,307.

SUMMARY OF THE INVENTION

The present invention overcomes the problems and disadvantages associated with current strategies and designs and provides novel methods and test indicators for determining the effectiveness of a sterilization procedure or measuring a parameter of the sterilization process.

One embodiment of the invention is directed to test indicators containing a biological material separated from the sterilizer environment by a cap. In addition, the cap may comprise one or more apertures to control access of the sterilizing medium to the biological material while preventing any biological material from being displaced from the test indicator. In another embodiment, the cap may have a sterilant permeable insert, such as a screen, membrane or mesh, covering one or more apertures in the cap. In yet another embodiment, the cap may have at least one protruding member to prevent mobilization of biological material within a test indicator.

In still another embodiment, the sterility indicator may comprise a modified cap and a compressed, gas-permeable material or a compressed, gas-permeable material without a cap. The compressed material controls access of the sterilizing medium to the biological material within a test indicator. The compressed, gas-permeable material may be formed and inserted into a test indicator as described in Patent Application Ser. No. 09/184,352 and U.S. Pat. No. 5,870,885.

Another embodiment of the invention is directed to a test indicator for determining the effectiveness of a sterilization procedure. Test indicators comprise an outer container having liquid impermeable and substantially gas non-absorptive walls, at least one opening leading into a chamber which contains one or more components of an interactive enzyme system, and a liquid impermeable or liquid semi-permeable gas-transmissive barrier between the components and the opening. These components may be fixed to a solid support or free-floating in a non-aqueous or partially-aqueous solution. After sterilization, the user simply mixes the components in the container with the remaining components of the enzyme system. If any enzyme activity is present, the enzymes plus any necessary coenzymes, cofactors and catalysts will interact with the substrate forming detectable product which can be assayed to determine the effectiveness of the sterilization procedure.

In one embodiment, the remaining components of the enzyme system may be in a separate container and may be transferred from the separate container to a test indicator by a user. In another embodiment of a test indicator comprising a cap with at least one protruding member, the at least one protruding member may contain the remaining components of the enzyme system, including, but not limited to, an indicator solution or growth medium.

Another embodiment of the invention is directed to methods for determining the efficacy of different types of sterilization processes. The test indicator consists of a plurality of interactive enzymes in a container with at least one opening. The opening is either filled with a compressed cylindrical foam insert, or the test indicator is covered with a modified cap, or a combination thereof. The test indicator is placed into the sterilization chamber. The foam insert, modified cap, or both, regulate the amount of sterilant such as steam, gas, chemicals or plasma entering the test indicator to achieve a response that can be equivalent to indicators containing bacterial spores. After the sterilization cycle is complete, the foam insert, if one is present, is removed and the remaining components of the enzyme system are combined. If the proper sterilization conditions were not met, the interactive enzyme system remains active, and a color product forms upon the addition of the remaining components of the enzyme system. If the proper sterilization conditions were met, the sterilant has destroyed components of the interactive enzyme system and no color product is formed. Inactivation of the enzyme system parallels the inactivation of bacterial spores subjected to the sterilization process. Results are available in from a few seconds to a few hours.

Another embodiment of the invention is directed to methods for adjusting the sensitivity of sterility indicators of the invention to one or more predetermined environmental parameters. Test indicators, substantially identical to the sterility indicators, are exposed to a sterilization procedure and the effectiveness of that procedure determined. The position and/or composition of the gas-transmissive plug of another test indicator may be adjusted and the another test indicator is exposed to the sterilization process. From the effectiveness of each test indicator for reacting to the environmental parameter, the sensitivity of the sterility indicator can be accurately and quantitatively adjusted.

Another embodiment of the invention is directed to methods for creating a challenging environment for the penetration of sterilant. Using an enzyme, spore or chemical indicator in a container with a controlled volume of gas-permeable material for creating a reproducible resistance for the sterilant penetration, a test pack for evaluating sterilant penetration or air removal is created.

Other embodiments and advantages of the invention are set forth, in part, in the description which follows and, in part, will be obvious from this description or may be learned from the practice of the invention.

DETAILED DESCRIPTION OF THE INVENTION

As embodied and broadly described herein, the present invention is directed to test indicators containing controlled volumes of compressed, gas-permeable material, a cap, or a combination thereof, for determining the effectiveness of a sterilization procedure and to methods for using the test indicators.

Conventional sterility indicators typically comprise viable spores which are exposed, along with the objects to be sterilized, to a sterilizing condition. After exposure, the indicator is removed and the spores cultured under defined conditions. Culturing takes days to a week for any sort of definitive results. Indicators often require post-sterilization incubation at higher than ambient temperatures to provide detectable results.

It had been discovered that indicators comprising enzymes and preferably interactive enzyme systems are a suitable substitute for spores. Inactivation of an enzyme system by a sterilization process mimics the death of viable spores. It has also been discovered that either an insert design comprised of a compressible material such as foam, a cap that may comprise one or more apertures, and/or a sterilant permeable insert, and/or at least one protruding member, or a combination thereof, provides accurate as well as reproducible results with these sterility indicators.

Indicators comprising multiple interacting enzymes and adjustable foam inserts and/or modified caps overcome the problems and disadvantages present with current strategies and designs for evaluating sterilization processes and can provide nearly instantaneous and reproducible results. The indicator system is simple to use and requires minimal training. Reliable results are achieved without specialized instructions or equipment. Surprisingly, indicators are also useful for monitoring many types of sterilization processes. In all cases, the results that can be achieved are rapid as well as reliable and reproducible.

One embodiment of the invention is directed to a test indicator device (the rapid sterility indicator or RSI) for the rapid determination of the efficacy of different types of sterilization processes (e.g., steam heat, dry heat, chemical sterilant, plasma). Indicators comprise either a compressible material placed as a plug into an opening or sleeve of a container wherein the container or sleeve has a smaller cross-sectional area than the cross-section of the article when not compressed, or a cap which may comprise one or more apertures, one or more sterilant permeable inserts, one or more protruding members, or a combination thereof. The container is made of non-adsorptive material such that the only pathway for the sterilant is through the foam insert and/or through the modified cap. That foam insert and/or cap regulate the amount of sterilant (e.g., steam, gas, chemicals or plasma) entering the test indicator and the amount of foam utilized may be regulated according to the sterilizing process. Indicator reagents are placed in the container with at least one opening and the opening is filled with the compressed cylindrical insert and/or the opening is covered with a modified cap. Many embodiments and advantages of a foam insert are described in U.S. patent application Ser. No. 09/184,352 and U.S. Pat. No. 5,870,885.

Because indicators are easily adjusted by varying foam insert volume or material, varying the number and size of apertures in a cap or cap material and thickness, or varying both a foam insert and cap, another advantage is that indicators can be modified to meet all major as well as minor alterations of a sterilization process. It is not necessary to switch to another type of sterilization indicator upon changing sterilization processes or sterilants. The insert and cap can be varied or either one can be omitted to optimize the sterility indicator and thereby meet multiple situations and different sterilants as well as different sterilization protocols. It is also not necessary to change the type of sterility indicator upon changing the sterilization process. As an adjustment can be as simple as changing the length of the plug, it is a very straight forward matter to implement a change during manufacture with little to no added expense.

Sterility indicators further contain spores, enzymes, an enzyme system or combinations thereof, as sensing reagents that provide an indication of sterility. These reagents may be a liquid or solid. Liquids are preferably in a non-aqueous or partially aqueous medium. Solids may be membranes such as disks and are preferably powders or tablets that contain granularized reagents. Such reagents can be made into a granulation by fluid-bed granulation. Fluid-bed granulation takes different components and coimmobilizes these components into clusters. Clusters comprise different components dried onto a seed particle. The granulation process begins by suspending a seed material in air and spraying a liquid material onto the seed. Other components are added either to the liquid solution or to the fluidized particles. Particles adhere to the liquid and form clusters of different components and, finally, moisture is removed from the clusters. The granulation process can be used to manufacture enzymes coimmobilized in a granulation or pressed into a tablet with little moisture as enzymes are typically most stable when packaged without water.

Granulation begins with a dry powder, referred to as the seed, which functions as a solid support. Seed material can be an inert substance or one of the components of the granulation and is placed into the process chamber. Controlled airflow into the chamber creates an air suspension of the particles and, thus, particles are suspended or fluidized. Once the particles are suspended in the air, a liquid solution is sprayed onto the solid particles.

The humidity, temperature and air velocity are controlled in the chamber. Humidity is kept very low and the temperature is increased to approximately 35° C. The liquid, after being sprayed onto the seeds, evaporates and a granulation is formed. Seeds are coated with the different ingredients forming the clusters and water is removed.

There are several ways two enzymes can be formed into a granulation product. For example, each enzyme can begin as a liquid solution. Using an inert solid seed material such as cellulose, one enzyme is sprayed onto the fluidized cellulose seeds. A second granulation is made of the second enzyme and the two granulations are blended together. Alternatively, the two enzymes could be mixed together as one liquid solution and sprayed onto the seed material. Alternatively, one or both enzymes could begin as a solid material. The solid material would be used as the seed material and a liquid binder solution is sprayed onto the seeds. Liquid solution is needed to create granulation and the solid, dry components adhere to the liquid solution. While the material is being fluidized, the high temperature and low humidity remove water from the granulation product and the enzymes are coimmobilized onto the seed material.

Granulations can also be pressed into tablets. For example, several granulations can be blended together using mechanical blenders and pressed into a single tablet. When working with several granulations, each can be tested for activity and then the final composition of the tablets activity can be adjusted by altering the amounts of each granulation component. The final enzyme tablet will contain very little water, typically less than about 5% and preferably less than about 3%.

Indicator reagents suitable for some applications comprise a single enzyme, such as that described in U.S. Pat. No. 5,073,488, along with the substrates, reagents, catalysts, co-factors, etc., necessary to produce a detectable product. Indicator reagents may also comprise multiple components of an interactive enzyme system. The enzyme system preferably comprises a known mix of enzymes, coenzymes, catalysts, cofactors, substrates, other reaction reagents or combinations such as those provided in U.S. Pat. No. 5,486,459. Enzyme systems comprise a plurality of enzymes that rapidly catalyze a series of coupled reactions which together produce a detectable product.

Another embodiment of the invention is directed to a method for determining the effectiveness of a sterilization process. The basic process comprises subjecting at least one and preferably multiple components of an enzyme system to a sterilization procedure. The enzyme system comprises a known mix of enzymes, coenzymes, catalysts, cofactors, substrates, other reaction reagents or combinations thereof, which is housed in a test indicator. The components have an interdependent activity which correlates with the viability of the microorganisms used in state-of-the-art biological indicators.

According to this method, a test indicator is placed into the sterilization chamber and subjected to a sterilization process. After the sterilization cycle is complete, the foam insert and/or cap may be removed and the remaining components of the enzyme system added to form a mixture. The cap may be replaced if desired. The mixture is incubated, if necessary, for a period of time sufficient to allow for product formation from the interaction of the enzymes with the substrate. Incubation times range from a few seconds to a minute and are preferably less than about 15 minutes, more preferably less than about 10 minutes and even more preferably less than about 3 minutes. If desirable, incubation can be eliminated and the product detected almost immediately or in less than about 20 seconds. A detectable product will form if all of the components of the enzyme system, including the plurality of enzymes, are present and active. A positive result is observed when each exposed component survives denaturation and is able to function interactively to produce a detectable enzyme-modified product. The enzyme-modified product as an indicator of residual activity is visually detectable within 1 to 60 minutes and preferably within seconds. Any change detected, which is preferably a color change, is an indication to an observer that the sterilization cycle had not inactivated certain components and, thus, was insufficient to assure sterilization of other articles exposed to the sterilization procedure. Conversely, an absence of a color change indicates that the sterilization procedure had inactivated at least one of the components thereby preventing the interactive reaction from taking place and thus, an equivalent of rapidly and directly detecting the survivability of bacterial spores in a similar conventional test.

Lack of detectable enzyme-modified product within the established period of time indicates a sterilization cycle which has been lethal to the function of the interactive enzyme system as well as lethal to a viable $10^6$ population of *Bacillus stearothermophilus* spores. Generally, these values are expressed as D-values, which is the time taken at a given temperature to reduce the viable population of test microorganisms to ten percent of its original value. Inactivation of the enzyme system parallels the inactivation of bacterial spores subjected to the sterilization process, except that the result may be available in minutes or seconds as compared to at least overnight incubation required for detection of bacterial growth from spores.

Product can be detected using a variety of procedures. For example, substrate can be labeled and the resulting radioactivity or enzymatic, electrical or fluorometric activity of the product detected using conventional devices such as, for example, those utilized for determining the effectiveness of sterilization procedures. Preferably, product is detected visually as visual detection is simple and inexpensive requiring little training and no specialized instrumentation outside of what would be found in a typical working environment.

The relationship between the components is very relevant to a determination of sterility because it is not simply a chemical or enzyme reaction, but an enzyme interaction reflective of the presumptive physiological state of microorganisms within the chamber. The ability of the methods of the invention to rapidly determine the efficacy of a sterilization cycle is based upon the discovery that the survival of functional capability of an enzyme system is necessary for the production of an enzyme-modified product. The rapidity of formation of the enzyme-modified product from the interacting enzymes is due, at least in part, to coimmobilization wherein the close proximity of two or more components of the enzyme system on a common solid support such that diffusion controlled exchange with bulk solution is limited. This process is further supplemented by component channeling or, the bringing together of two or more components of sequential reactions at a surface or microenvironment to further limit diffusion-controlled exchange with bulk solution. Component channeling with regard to enzymes is described in I. Gibbons et al. (Meth. Enzymol. 136:93–103, 1987).

The ability of the components of an enzyme system to survive conditions which only partially kill test microorganisms is dependent, at least in part, upon the use of a semi-permeable barrier between the sterilant and the enzymes, and that the interactive enzyme system will remain active following a sterilization cycle which is insufficient to kill the test microorganisms. It is not necessary that the barrier be impermeable to microorganisms such as bacteria, only that it, be fluid permeable to permit exposure of the indicator components to the sterilizing environment. Such as through open cells of a compressible material or around the sides of a closed cell compressible material. This provides a direct correlation of spore viability with the interactive activity of the enzymes of the system which, following an inadequate sterilization cycle, is sufficient to convert a substrate system for those enzymes to a visually detectable concentration of product within a relatively short time, preferably 1 to 60 minutes. The basis for the correlation between the activity of the enzymes and other components to the germination and growth of microorganisms is due to the commonality of both in their reliance upon systems of biologically derived interacting enzymes and coenzymes to function. The sterility indicator demonstrates that there is a direct correlation between the conditions to kill a microorganism and the conditions to inactivate a component of a network of interacting enzymes. In fact, the interactive system can be considered to mimic a bacterial spore in that there is a semi-permeable membrane, the spore wall, that encases a collection of interactive enzymes. In the case of an amplification interactive enzyme system, if any one of the key enzymes, coenzymes, cofactors, substrates, catalysts, or other reagent components of the system are totally inactivated when an indicator solution is added, no color change will occur, thus, mimicking conventional spore systems, but able to provide results at much faster speeds.

Using the test indicators of the invention, sterility verification is determined from completion of the test results which, surprisingly, can be very rapidly achieved because the reliability of conventional biological indicators is combined with the speed of techniques closer to that utilized by enzymatic and chemical indicators. Further, and unlike spores, resistance is correlated with activity, and in enzyme systems containing enzymes, coenzymes, catalysts, substrates or other reagents of an interactive system, stability can be very precisely quantitated individually as well as in multiple enzyme systems. Therefore, using interactive enzyme systems not only is speed increased, but a level of standardization can be achieved which is far superior to that obtained with conventional biological or other enzymatic techniques.

Another embodiment of the invention is directed to methods for the manufacture of adjustable indicator systems for the determination of the effectiveness of sterilization processes using steam, gas, radiation, chemical and plasma sterilizers, which are used in many hospitals, laboratories, and clinics, as well as in research institutions, in food and environmental laboratories, and in all technologies which utilize sterilization in manufacturing, production or waste disposal.

Sensitivity of sterility indicators can be adjusted quickly and easily for the manufacture of sterility indicators reactive to one or more predetermined parameters. For example, a test indicator substantially identical to the sterility indicator is exposed to a sterilization procedure and the effectiveness of that test indicator for reacting to the predetermined environmental parameter determined. The position and/or composition of the, for example, gas-transmissive plug of another test indicator is adjusted and another test indicator is exposed to the sterilization process. From the results determined for each test indicator, the sensitivity of the sterility indicator can be adjusted to optimize detection to the specific environmental condition or conditions.

Adjustments can be as simple as repositioning the gas-transmissive plug such as, for example, by extending or retracting an overhang portion of the plug, or by altering the composition of the plug by, for example, increasing or decreasing plug density, pore size or composition. The overhang portion could be extended to increase sensitivity of the indicator to a combination of increased temperature, humidity and pressure. A plug comprised of a compressible material can be adjusted by increasing the density of the compressible material to decrease sensitivity of the indicator to a combination of increased sterilant, chemicals, temperature, humidity and pressure. Likewise, a cap can be modified in thickness, the number of apertures, the type of sterilant permeable insert, the size, shape, and number of protruding members, or a combination thereof.

A sterility indicator includes a biologically relevant material, such as bacterial spores or preferably a source of multiple interacting enzymes, in a container having a liquid impermeable and substantially gas non-adsorptive wall and at least one opening filled or covered with a gas-transmissive barrier, said opening leading into a chamber which contains one or more components of the interactive enzyme system, with the gas-transmissive barrier between the a components and the opening. The container may be any shape including, but not limited to, spherical, cubic, pyramidal, or preferably cylindrical. Interacting components are preferably localized within close proximity to one another such as within the matrix of a cellulose filter disk or granulation product, and/or within a defined medium and are thus, coimmobilized. One or more enzymes, substrates, coenzymes or catalysts may be included on the solid matrix. Within the container, or covering the container, is an effective amount of a gas-transmissive material to form the barrier which is semi-permeable, but not freely or wholly permeable to the transmission of liquids and gases, and an effective means for maintaining a finite distance between the semi-permeable opening and the enzymes.

In another embodiment, a sterility indicator includes a biologically relevant material, such as bacterial spores or preferably a source of multiple interacting enzymes, in a container having a liquid impermeable and substantially gas non-adsorptive wall and at least one opening covered with a cap, the opening leading into a chamber which contains one or more components of the interactive enzyme system. Interacting components are preferably localized within close proximity to one another such as within the matrix of a cellulose filter disk or granulation product, and/or within a defined medium and are thus, coimmobilized. One or more enzymes, substrates, coenzymes or catalysts may be included on the solid matrix. The cap is made of a porous plastic material or has a plurality of apertures, or is both made of a porous plastic material and has a plurality of apertures, to permit the transmission of liquids and gases through the at least one opening.

Figure 1A:
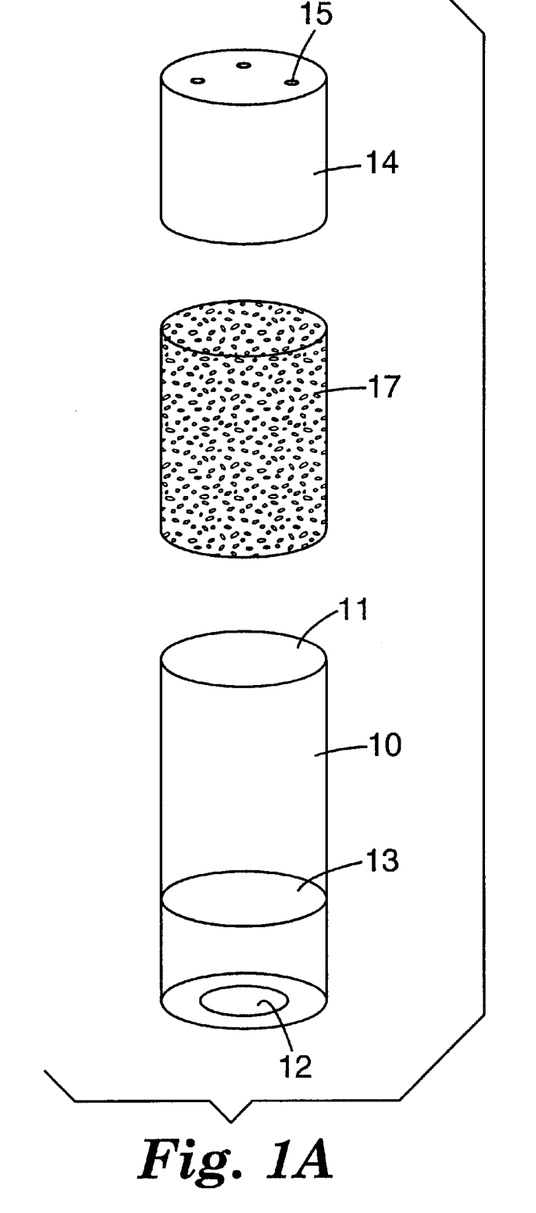
FIG. 1A Diagram of the components of a container for a rapid sterility indicator.
Figure 1B:
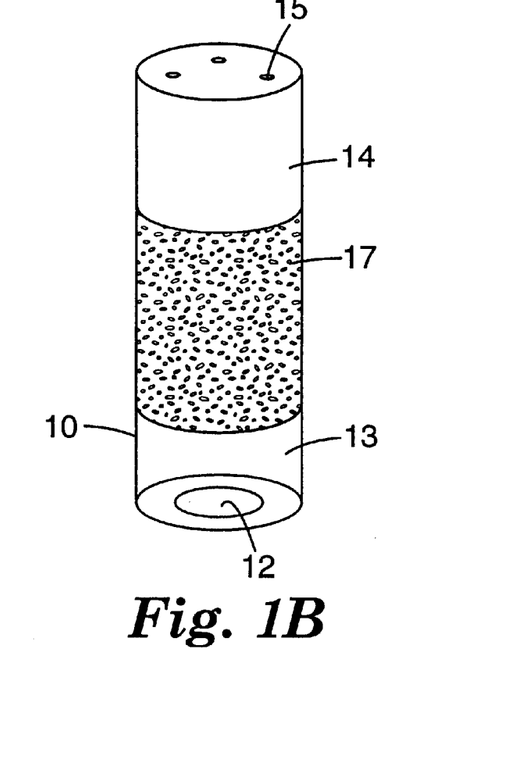
FIG. 1B Diagram of the construction of a completed rapid sterility indicator.

A rapid multiple enzyme sterility indicator of the invention is illustrated in FIG. 1A and FIG. 1B. The indicator comprises cylindrical tube 10 having liquid impermeable walls with single opening 11 at one end. Cylindrical tube 10 contains solid support disk 12 upon which multiple interacting enzymes are coimmobilized. Cylindrical tube 10 also contains non-aqueous medium 13 covering solid support disk 12. Single opening 11 is covered with cap 14 having a plurality of apertures 15 allowing unimpeded access of sterilant through single opening 11. The apparatus of FIG. 1A and FIG. 1B is assembled by placing solid support disk 12, upon which multiple interacting enzymes are coimmobilized, into the bottom of cylindrical tube 10. Non-aqueous medium 13 is added to cover solid support disk 12. A cylinder of heat resistant foam material 17 is compressed into cylindrical tube 10 providing a structural framework for the containment of non-aqueous medium 13. Foam material 17 also serves to maintain a fixed distance between the multiple interacting enzymes coimmobilized upon solid support disk 12 and single opening 11. Cap 14 is placed on top of cylindrical tube 10 covering single opening 11.

Figure 2:
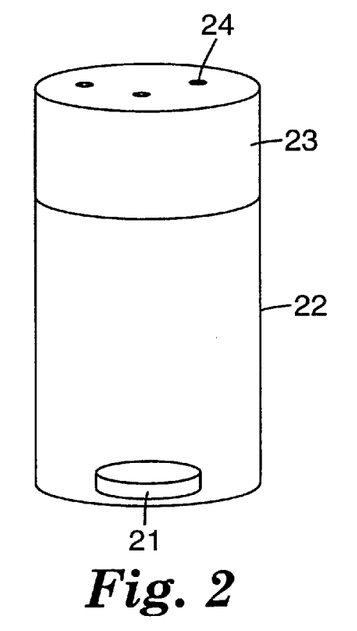
FIG. 2 A preferred embodiment of a rapid sterility indicator unit.

A preferred indicator unit of the invention is the rapid-multienzyme sterility indicator shown in FIG. 2. This multiple-enzyme sterility indicator comprises a test unit and indicator solution. The test unit is comprised of chamber 22 having liquid impermeable walls with an opening at one end. Chamber 22 contains granulized tablet 21 comprising coimmobilized interacting enzymes. The opening of chamber 22 is covered with a cap 23 having at least one aperture 24 allowing access of sterilant through the opening.

Figure 2A:
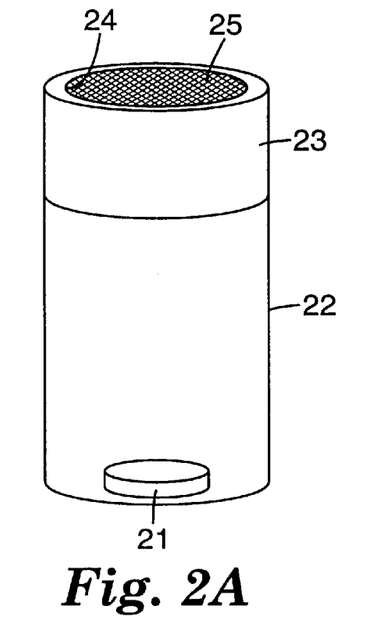
FIG. 2A An embodiment of a rapid sterility indicator unit with a cap comprising a sterilant permeable insert.

In another embodiment of a preferred indicator unit of the present invention, the opening of chamber 22 is covered with a cap 23 having at least one aperture 24, as depicted in FIG. 2A. The at least one aperture 24 comprises at least one sterilant permeable insert 25 which may be attached to the bottom or top surface of the cap 23, inserted into the cap 23, or place directly on top of, or in, the opening to chamber 22. The sterilant permeable insert allows access of sterilant through the opening of a chamber 22 while preventing granulized tablet 21, or any other essential material, from falling out of the chamber. The sterilant permeable insert may be a screen, a membrane, a mesh, a combination thereof, or any insert that one of skill in the art may find to be permeable to sterilant while being impermeable to materials which should remain within the chamber 22.

Figure 2B:
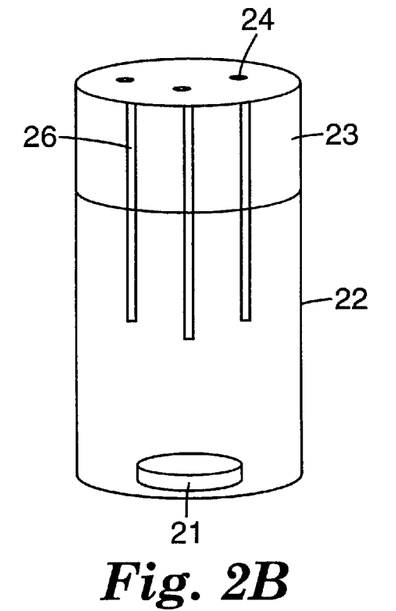
FIG. 2B An embodiment of a rapid sterility indicator unit with a cap comprising protruding members.
Figure 2C:
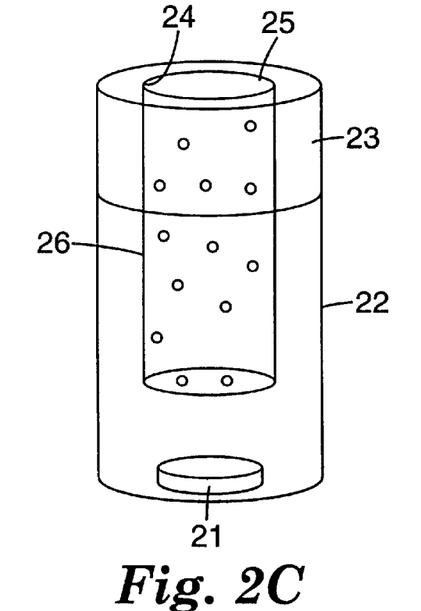
FIG. 2C An embodiment of a rapid sterility indicator unit with a cap comprising a hollow protruding member with apertures therein.

In yet another embodiment of a preferred indicator unit of the present invention, a cap 23 having at least one aperture 24 may comprise at least one protruding member 26, as depicted in FIG. 2B and FIG. 2C. The at least one protruding member 26 prevents a granulized tablet 21, or any other essential material, from being displaced from chamber 22. The protruding member may be a wand, a stem, a hollow member, a solid member, a combination thereof, or any appropriate member known to one of skill in the art. The at least one protruding member 26 may be made of a similar or different material as the cap and may be attached to the cap or to the opening of the chamber. As depicted in FIG. 2C, a hollow protruding member 26 may further be meshed, comprise apertures, or be made of a permeable material to allow access of sterilant through protruding member 26 into chamber 22.

Figure 3A:
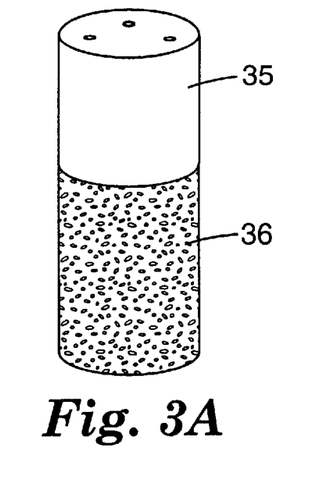
FIG. 3A Diagram of a sterility indicator.
Figure 3B:
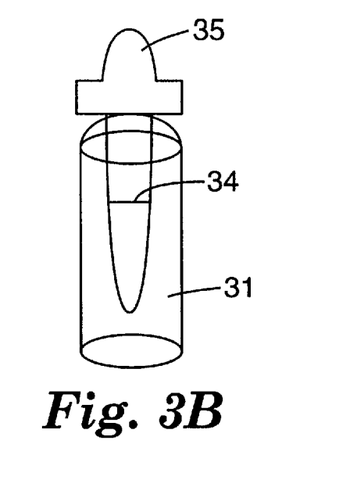
FIG. 3B Diagram of a bottle of indicator solution.
Figure 3C:
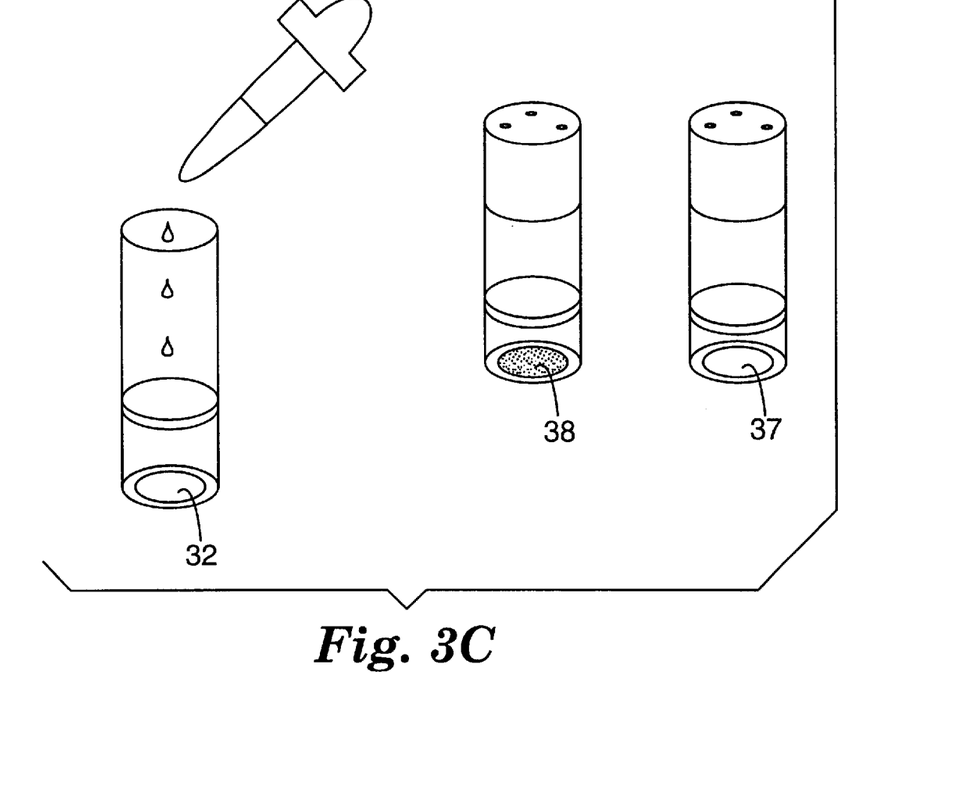
FIG. 3C Diagram of a preferred operation of a multiple-component container of a rapid sterility indicator.

The dispenser of the indicator solution is shown in FIG. 3A, FIG. 3B, and FIG. 3C. A bottle contains indicator solution 31 which produces a visual color change when added to active multiple interacting enzymes coimmobilized on solid support disk 32. The bottle contains eyedropper 33 with premeasured volume line 34. Filling eyedropper 33 to premeasured volume line 34 with indicator solution 31 assures that the correct volume or number of drops of solution, is dispensed into the tube.

A method for conducting the sterility test is also illustrated in FIG. 3C. The sterility indicator is placed into the sterilizer along with other materials which are to be sterilized. The sterility indicator is exposed to the sterilant during the course of a sterilization cycle. After the completion of the sterilization cycle, the sterility indicator is removed from the sterilizer and allowed to cool to room temperature. Cap 35 and foam material 36 are removed and can be safely discarded. Indicator solution 31 is drawn into eyedropper 33 using the premeasured volume line 34 to assure that the correct volume of indicator solution is used and dispensed into the tube. The resulting mixture is incubated, if necessary, at room temperature for seconds to minutes, preferably for less than about 10 minutes and more preferably for less than about 3 minutes. The solid support disk is visually inspected at the end of the incubation period. An absence of red coloration on the solid support disk (e.g., white) indicates negative result 37 and signifies a successful sterilization cycle. The presence of red coloration on the solid support disk indicates positive result 38 and signifies an unsuccessful sterilization cycle.

Figure 4:
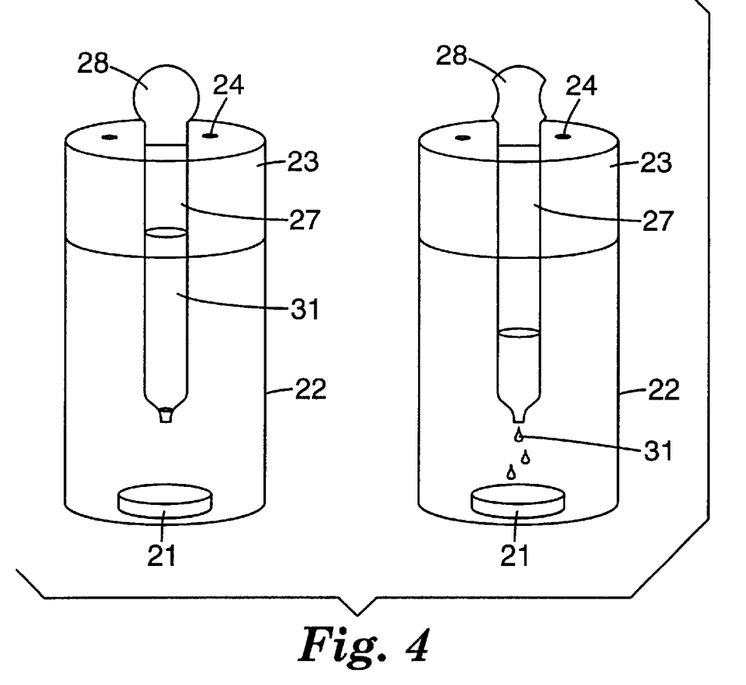
FIG. 4 Diagram of a preferred operation of a rapid sterility indicator with a cap comprising a protruding member that contains indicator solution.

Another embodiment of a sterility indicator unit of the present invention is demonstrated in FIG. 4. The sterility indicator in this embodiment may comprise a wand member 27, or a plurality of wand members, protruding into chamber 22. Wand member 27 may be hollow or solid and may be made of any appropriate material including, but not limited to, plastics, ceramics, or glass. In a further embodiment, the wand member 27 may contain a quantity of indicator solution 31, or any other substance that may be a useful component of a sterility indicator system including, but not limited to, growth medium. In an embodiment comprising a plurality of wand members, each wand member may comprise quantities of different components for use in a sterility indicator system. Each wand member 27 may further comprise a dispensing member 28. The dispensing member 28 may be made of any appropriate material including, but not limited to, plastic, rubber, or silicates. In one embodiment, dispensing member 28 may be shaped like a pipette end; in another embodiment, a dispensing member may be breakable membrane. If dispensing member 28 comprises a breakable membrane, the membrane may further be cross hatched to facilitate breaking. In yet a further embodiment, a sterility indicator may have a cap 23 covering the opening of the chamber 22. The cap 23 may further comprise at least one aperture 24. Wand member 27 may be inserted through the cap 23 or may be attached to a surface of the cap 23.

In an exemplary method for conducting a sterility test using an embodiment of the invention comprising at least one wand member 27, a sterility indicator is placed into a sterilizer. The sterility indicator is exposed to sterilant for an appropriate period of time. The sterility indicator may be removed from the sterilizer and allowed to cool to room temperature. A dispensing member 28 may be squeezed, crushed, or broken to dispense indicator solution 31 into chamber 22. The resulting mixture may be incubated, if necessary, at room temperature for seconds to minutes, preferably less than about 10 minutes and more preferably for less than about 3 minutes. Granulized tablet 21 may be inspected at any pre-determined appropriate time after addition of indicator solution 31. An absence of a color change on the granulized tablet 21 indicates a negative result and signifies a successful sterilization cycle. The presence of a color change (i.e. to red) indicates a positive result and an unsuccessful sterilization.

The sterilization procedure useful in the practice of the invention may be, for example, a steam-pressure procedure or autoclaving (121° C. or higher, such as 132° C. or 134° C.), a chemical procedure utilizing ethylene oxide or another appropriately lethal chemical or dry heat of temperatures between about 50° C. to about 200° C., or a plasma-phase sterilization procedure. These procedures are practiced in the health care industry, but also in industries having to do with environmental technology, food manufacturing, waste disposal and in those a technologies where sterility is required.

Another embodiment of the invention is directed to an indicator for determining the effectiveness of a sterilant to pass through a tortuous path such as a challenge pack. Challenge pack testing, can make use of the same design and the same adjustable features. An AAMI steam challenge pack consists of a biological indicator such as bacterial spores on an inert carrier, wrapped in 16 surgical towels. The towels create a tortuous path for the steam to reach the indicator. This simulates the wrapped goods processed in a steam sterilizer in a hospital setting.

Challenge packs are used to test the effectiveness of the sterilant to pass through the pack and reach the indicator.

Figure 5:
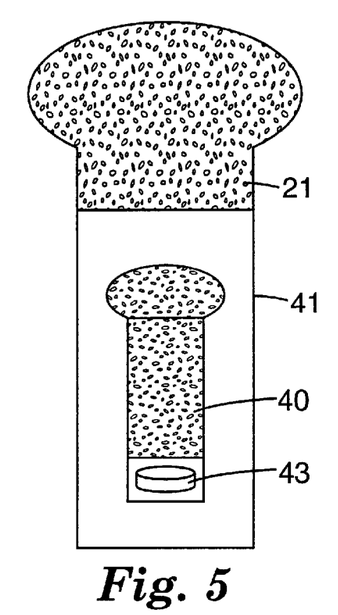
FIG. 5 Diagram of one embodiment of a challenge pack.

This simulates wrapped goods processed in the sterilizer. A foam insert design or a modified cap design can be used for challenge pack testing. A sterility indicator, either the enzyme-based indicator described previously or a conventional spore-based indicator may be used in this type of challenge pack. An example of a challenge pack is shown in FIG. 5.

Sterility indicator 40 is placed into container 41 which has at least one opening filled with a predetermined amount of foam 42. Container 41 has substantially gas non-adsorptive walls so the sterilant has to enter through foam 42 to reach sterility indicator 40 and thereby regulates the amount of sterilant entering the container. Sterility indicator 40 contains either spores or enzymes 43. Foam 42 regulates the amount of steam or sterilant entering the container. After the challenge pack has been exposed to the sterilization process, the indicator is removed from the challenge pack and processed. If the indicator is positive, proper sterilization conditions were not achieved within the pack. A negative result means proper conditions were met. The rapid sterility indicator described above or a standard biological indicator can be used in conjunction with the challenge pack. The challenge pack is simple to use and provides reproducible results. The desired amount of challenge can be easily reproduced to mimic the challenge described by standards such as AAMI, ISO or EN for a steam or ethylene oxide challenge pack.

Figure 6:
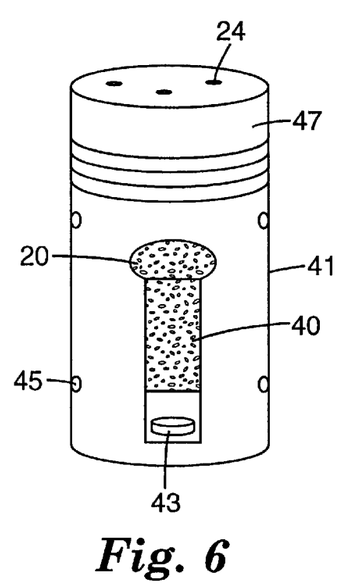
FIG. 6 Diagram of another embodiment of a challenge pack.

As depicted in FIG. 6, container 41 of the challenge pack described above may have a cap, such as screw cap 47, placed over the at least one opening instead of foam, or may have both a cap and foam. The cap may be made of a porous plastic material, may have one or more apertures 24, may be both made of a porous plastic material and have one or more apertures, or made be made of an impervious material with no apertures. Additionally, container 41 may have one or more apertures 45 in its wall. If the challenge pack has a cap made of an impervious material with no apertures, than the container has one or more apertures 45 in its wall. The sterility indicator 40 which is placed in the container may have a cap placed over the at least one opening or may have a foam insert 20 installed in the at least one opening, or may have both a cap and foam. The cap may be made of a porous plastic material or may have a plurality of apertures, or may be both made of a porous plastic material and have a plurality of apertures. The porous plastic material is preferably a non-absorptive plastic that can withstand multiple exposure to sterilization.

Another embodiment of the invention is directed to the foam insert design for the air removal test. The air removal test consists of a container with a Bowie-Dick test sheet or a chemical indicator on a carrier. The transparent container consists of at least one opening which is filled with foam. After the test cycle is complete, the air removal test is removed from the sterilization chamber. The user observes the uniformity of the color change of the chemical indicator. Since the material of the container is transparent, the user would simply observe the uniformity of the chemical indicator ink. Thus, there is no need to unwrap the device.

The air removal test is also based on the similar design. By placing a chemical indicator into a transparent container with a foam insert, the prevacuum air removal test equivalent is made. The air removal test is placed into a prevacuum steam sterilizer. After the cycle is complete, the user can simply view the uniformity of the color change of the chemical indicator in the transparent container or simply open the container and remove the chemical indicator.

The foam insert design and the modified cap designs overcome many disadvantages of the current designs for testing the effectiveness of sterilization processes. Both the foam insert and cap designs can be used as a component of a rapid sterility indicator composed of interactive enzyme systems which can provide nearly instantaneous results. A sterility indicator with a foam insert or modified cap design also offer the advantage of being adjustable to suit various types of sterilization processes. Presence of foam, a cap made of porous material and/or comprising apertures of various size and quantity, or a combination thereof, also allows the sterility indicator to effectively control the amount of sterilant entering the device in a standardized manner. The enzyme content of the rapid sterility indicator and the foam and cap specifications can be easily controlled to provide reproducible results during manufacturing. Conventional biological indicators that are based on the inherent resistance of bacterial spores can not be as easily controlled.

The foam insert design described in U.S. Pat. No. 5,870,885 also overcomes disadvantages of challenge pack and air removal test designs. Assembly of AAMI test packs is very time consuming. AAMI packs are not standardized in the sense that differences in how individuals make the packs and different types of towels can result in packs with differing characteristics. The advantages of the foam insert design is that it can be used for a sterility indicator for many types of sterilizers as well as challenge packs and air removal tests, it is simple to use and it is standardized and reproducible. The fact that the same design can be used for multiple tests (e.g., sterility, challenge packs, air removal) offers simplicity to the users. The challenge pack and air removal test designs also allow the user to quickly and easily retrieve the indicator. There is no need to unwrap many towels to retrieve the indicator. The transparent container also permits the user to confirm that an indicator is present in the pack.

Figure 7:
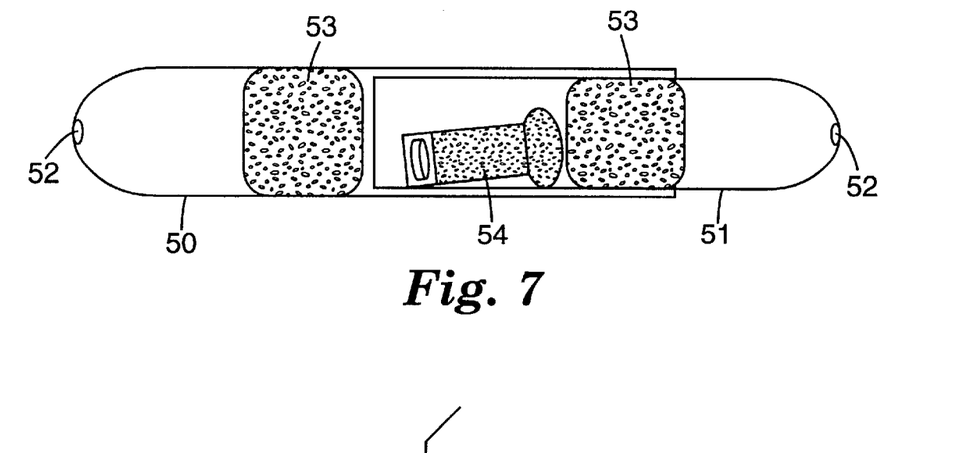
FIG. 7 A two container design challenge pack.

Another embodiment of the invention is directed to a method for determining the effectiveness of a sterilant to pass through a tortuous path comprises a challenge pack that employs the foam and container design that allows the users to easily open and close the challenge pack for repeated use. The challenge pack consists of two containers, two foam inserts and a sterility indicator, as shown in FIG. 7. Each container has at least two openings, one opening is the same size as the diameter of the container, the second opening is much smaller. One container 50 has a slightly larger diameter than the other container 51. Each container has a small aperture 52 opposite the larger opening and a piece of foam 53 placed near the small opening. A sterility indicator 54 is placed into the smaller diameter container and the second container with a slightly larger diameter is placed over the first container's large opening. The containers fit together tightly due to their similar diameters. Instead of relying on the similar diameters to hold the two tubes together, a screw closure, a snap locking device or a twist locking device could be used. The containers have substantially gas non-adsorptive walls so that the sterilant has to enter through small apertures 52 and pass through the foam inserts 53 to reach sterility indicator 54.

After the challenge pack has been exposed to the sterilization process, the two containers are dislodged from one another and the indicator is retrieved and processed as usual. This test pack can be used again by placing an unexposed indicator into one of the containers and replacing the second container over the first container as shown in FIG. 7. The sterility indicator can be the enzyme-based indicator or a conventional spore-based indicator.

Another embodiment of a reusable challenge pack design consists of a single container with one opening and a cap. A sterility indicator is placed into the container. The cap is made from a porous plastic material which allows steam to pass through. The capping device can be easily opened and closed by the user to retrieve the exposed indicator and add an unexposed indicator for the next test. The materials are a non-absorptive plastic which can withstand multiple exposures to sterilization.

Figure 8A:
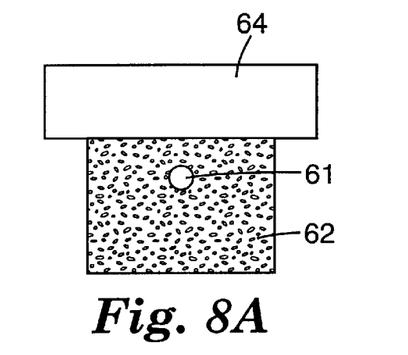
FIG. 8A Diagram of an assembled rapid sterility indicator test unit challenge pack design.
Figure 8B:
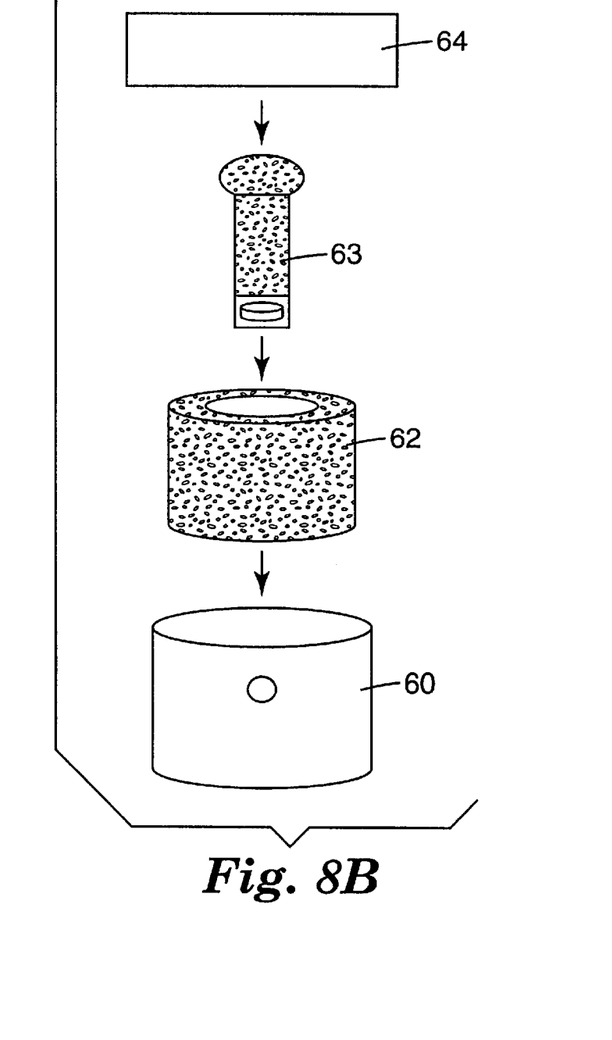
FIG. 8B Diagram of the components of a rapid sterility indicator test unit challenge pack design.

Another embodiment of a reusable challenge pack designs comprises a single container with a closure device, foam and a test indicator as shown in FIG. 8A and FIG. 8B. The bottom portion of cylindrical container 60 has two apertures 61 in the sides of the container. Tubular foam insert 62 fits tightly into the container. Foam insert 62 has an aperture in the center which conforms to the shape of sterility indicator 63 which fits tightly into foam insert 62. Screw cap 64 is placed over the large opening of the container. When screw cap 64 is secured onto the container containing sterility indicator 63, sterilant would pass through the small openings in the sides of the container and through foam insert 62, before reaching sterility indicator 63. This is a tortuous path for the sterilant. This design would perform equivalent to other challenge packs. The materials are a non-absorptive plastic which can withstand multiple exposures to sterilization. The sterility indicator can be the enzyme-based indicator or a conventional spore-based indicator. By using a larger container and corresponding larger foam insert and replacing a chemical indicator (test sheet covered with unexposed chemical indicator ink) for the sterility indicator, this design could be used for air removal tests in pre-vacuum sterilizers. After processing in a pre-vacuum sterilizer, the uniformity of the chemical indicator color change would be used to determine if any air was present in the chamber. If air was present, the color change of the chemical indicator would not be uniform.

The following examples illustrate embodiments of the invention, but should not be viewed as limiting the scope of the invention.

EXAMPLES

Example 1

Rapid Sterility Indicator for Monitoring Steam Sterilization Process.

A rapid sterility indicator for steam sterilization is composed of a test unit and indicator solution. The test unit is composed of a cylindrical glass vial, a tablet containing components of a plurality of interacting enzyme systems, a foam insert, and a label. The glass vial is approximately ¼ inches in diameter and 1 inch high, open on one end.

The tablet containing two interactive enzymes of the enzyme system is placed into the vial. The tablet is a granulation of glucose dehydrogenase and diaphorase. The preferred enzyme concentration for each enzyme is 8 to 15 units per 20 mg tablet. The opening of the vial is filled with a compressed foam insert. The foam insert is preferably a cylinder, with a diameter range of ¼ to 1 inch, preferably approximately ½ inch and the length range to 3 inches preferably approximately 1½ inches in length. Foam is partially open celled with a density of approximately 6 pounds per cubic foot and the foam material is polyurethane. The detailed specifications include: polyester foam, open cell, 6 lbs, charcoal color, density is 5.00–6.60 p.c.f, strength 20.0–40.0 p.s.i., elongation 300–500%, tear resistance is 3.0–5.0 p.l.i., compress set 3.0 to 10.0%, load defection, 0.50 to 0.90 p.s.i., flammability HF-1, and cell size 50–70 c.d.i. On the outside of the vial was a label containing steam-sensitive indicator ink.

This test unit was placed into the sterilization chamber of a steam sterilizer operating at 121° C. along with the items to be sterilized. After the cycle is complete, the test unit was removed from the sterilization chamber. The color change of the steam-sensitive indicator ink serves to identify the processed units from unprocessed units. The foam insert was removed and five drops of the clear, colorless indicator solution was added to the vial containing the white enzyme tablet. The indicator solution was packaged in an amber glass bottle with a dropper dispenser. The indicator solution contains p-iodonitrotetrazolium violet within a range of 32 $\mu$M to 16 mM, preferably 3.2 mM; AND (-nicotinamide adenine dinucleotide) within a range of 1 $\mu$M to 5.5 mM, preferably 0.11 mM; glucose within a range of 1% to 90% preferably 10%; ethanol within a range of 1% to 95% (by volume), preferably 5.5%; citric acid within a range of 0.0032 mm to 3.2 m, preferably 17 mm. The preferred buffer was 0.05 M Tris, pH 6.0–8.5.

The predetermined survival cycle in a BIER vessel operating at 121° C. was 5 minutes, the kill cycle was 15 minutes for sterility indicators. Survival cycles were cycles with short exposure times in which indicators should test positive, indicating proper sterilization conditions were not met. Kill cycles were usually the standard cycles times in which the indicator should test negative indicating proper sterilization conditions were met. After indicator solution was added to the white tablet, the color of the tablet was visually observed for 1 to 20 seconds. After a 5 minute autoclave survival cycle at 121° C., which represents inadequate sterilization conditions, a positive result was expected and observed, in which the enzymes are active and a red colored product was formed on the surface of the tablet at or before 20 seconds. After a 15 minute autoclave kill cycle at 121° C. which represents an adequate sterilization cycle, a negative result was expected and observed, in which one or more enzymes were inactivated and no red colored product was formed. These positive and negative results parallel the results of bacterial spores exposed to similar conditions in a steam autoclave.

TABLE 1

Steam Sterilization Test in a BIER Vessel

|  | Survival Time (5 minutes) | Kill time (15 minutes) |
| --- | --- | --- |
| Rapid Sterility Indicator | 10/10 | 0/10 |
| Sportrol spore strips ($10^6$ *B. stearothermophilus*) | 10/10 | 0/10 |

Table 1 shows results from a typical experiment. Results are recorded as the number of positives over the number tested (121° C.) in a BIER vessel. Rapid sterility indicators provided both positive results after the survival cycles and negative results after the kill cycles. These results demonstrate the at least equivalence of rapid sterility indicators to conventional biological indicators.

Example 2

Prevacuum Sterilization.

An alternative sterilization protocol involves preevacuation of the sterilization chamber followed by a shorter period of exposure to steam at a higher temperature (132° C. or 134° C.). The predetermined survival/kill cycle times for a 132° C. and 134° C. pre-vac sterilizer is 20 seconds/3.0 minutes, respectively. Test units according to Example 1 were processed in the prevacuum mode, and the results are shown in Table 2.

TABLE 2

Steam Sterilization Test in a Prevacuum Sterilizer using 132° C. and 134° C. Steam

|  | Survival Time | Kill time |
|---|---|---|
| Rapid Sterility Indicators (132° C.) | 10/10 | 0/10 |
| Sportrol spore strips (132° C.) | | |
| ($10^6$ B. stearothermophilus) | 10/10 | 0/10 |
| Rapid Sterility Indicators (134° C.) | 10/10 | 0/10 |
| Sportrol Spore strips (134° C.) | | |
| ($10^6$ B. stearothermophilus) | 10/10 | 0/10 |

Results in Table 2 are recorded as the number of positives over the number tested. The indicator reaction was read at 20 seconds. These results show that the rapid sterility indicators met the predetermined survival/kill parameters for a 132° C. and 134° C. prevacuum steam sterilizer, at least equivalent to biological indicators. The Rapid Sterility Indicators, as described in Example 1, can effectively monitor both 121° C. gravity and 132° C./134° C. pre-vac sterilization cycles.

Example 3
132° C. Gravity Displacement Study Using Indicator System Comprising A Container Having a Cap as Depicted in FIG. 2A Three lots of Test Units were each subjected to 1.0, 1.25, 1.5, 1.75, 2.0, 2.25, 2.5, 2.75, 3.0, 3.25 and 3.5 minutes of 132° C. saturated steam in a gravity displacement BIER vessel. Following exposure, the Test Units were removed, the caps were unscrewed from the vials and Indicator Solution was added to the vial (a sufficient amount to cover the tablet). Results at 20 seconds were recorded as number of positive Test Units over number of Test Units tested.

Acceptance criteria required that all RSI Test Units yeild 100% positive results after one minute of exposure

TABLE 3

132° C. Gravity Displacement Inactivation Curve
RSI Rapid Indicator with Screw Cap

| | RSI Rapid Indicator | | |
|---|---|---|---|
| Exposure Time (minutes) | Lot GOT00[1] | Lot GOT0[2] | Lot GOT0[3] |
| 1.0 | 10/10 | 10/10 | 10/10 |
| 1.25 | 10/10 | 10/10 | 10/10 |
| 1.5 | 10/10 | 10/10 | 10/10 |
| 1.75 | 10/10 | 10/10 | 10/10 |
| 2.0 | 10/10 | 10/10 | 10/10 |
| 2.25 | 10/10 | 9/10 | 9/10 |
| 2.5 | 6/10 | 6/10 | 7/10 |
| 2.75 | 1/10 | 0/10 | 0/10 |
| 3.0 | 0/10 | 0/10 | 0/10 |
| 3.25 | 0/10 | 0/10 | 0/10 |
| 3.5 | 0/10 | 0/10 | 0/10 |
| 4.0 | * | * | * |
| 4.5 | * | * | * |
| 5.0 | * | * | * |

[1]Lot GOT00 consists of tablet lot 0-200-T-01, POREX lot 00621, Indicator Solution lot GOT00
[2]Lot GOT01 consists of tablet lot 0-35-T-01, POREX lot 00621, Indicator Solution lot GO501
[3]Lot GOT02 consists of tablet lot 0-200-T-01, POREX, Indicator Solution lot GOT02
*Cycles not performed at these exposure times.

Example 4
134° C. Gravity Displacement Study Using Indicator System Comprising a Container With a Cap as Depicted in FIG. 2A Three lots of Test Units were each subjected to 1.0, 1.25, 1.5, 1.75, 2.0, 2.25, 2.5, 2.75, 3.0, 3.25 and 3.5 minutes of 134° C. saturated steam in a gravity displacement BIER vessel. A Biological Indicator Evaluator Resistometer (BIER) is a saturated steam vessel intended for use in evaluating the resistance performance of biological indicators. The BIER vessel operates in compliance with ANSI/AAMI ST45-1992, BIER/Steam vessels. Following exposure, the Test Units were removed, the caps were unscrewed from the vials and Indicator Solution was added to the vial (a sufficient amount to cover the tablet). Results at 20 seconds were recorded as number of positive Test Units over number of Test Units tested.

Acceptance criteria required that all RSI Test Units yeild 100% positive results after one minute of exposure and 100% negative results after three minutes of exposure.

TABLE 4

134° C. Gravity Displacement Inactivation Curve
RSI Rapid Indicator with Cap

| | RSI Rapid Indicator | | |
|---|---|---|---|
| Exposure Time (minutes) | Lot GOT00[1] | Lot GOT0[2] | Lot GOT0[3] |
| 1.0 | 10/10 | 10/10 | 10/10 |
| 1.25 | 10/10 | 10/10 | 10/10 |
| 1.5 | 10/10 | 10/10 | 10/10 |
| 1.75 | 10/10 | 10/10 | 10/10 |
| 2.0 | 10/10 | 10/10 | 10/10 |
| 2.25 | 10/10 | 10/10 | 9/10 |
| 2.5 | 8/10 | 8/10 | 6/10 |
| 2.75 | 0/10 | 0/10 | 0/10 |
| 3.0 | 0/10 | 0/10 | 0/10 |
| 3.25 | 0/10 | 0/10 | 0/10 |
| 3.5 | 0/10 | 0/10 | 0/10 |
| 4.0 | * | * | * |
| 4.5 | * | * | * |
| 5.0 | * | * | * |

[1]Lot GOT00 consists of tablet lot 0-200-T-01, POREX lot 00621, Indicator Solution lot GOT00
[2]Lot GOT01 consists of tablet lot 0-35-T-01, POREX lot 00621, Indicator Solution lot GOT01
[3]Lot GOT02 consists of tablet lot 0-200-T-01, POREX lot 00718, Indicator Solution lot GOT02
*Cycles not performed at these exposure times.

Other embodiments and uses of the invention will be apparent to those skilled in the art from consideration of the specification and practice of the invention disclosed herein. All U.S patents and other documents referenced herein, for whatever reason, are specifically incorporated by reference. It is intended that the specification and examples be considered exemplary only, with the true scope and spirit of the invention being indicated by the following claims.

We claim:

1. A test indicator for determining the effectiveness of a sterilization procedure comprising:
   a container having at least one opening communicating with an interior chamber containing biological material to be used as an indicator of destruction of living organisms by the sterilization procedure;
   a cap that provides direct access to the biological material, wherein the cap is positioned on the at least one opening such that movement of gas between the environment surrounding the test indicator and the interior chamber occurs through the cap.

2. The test indicator of claim 1 wherein the cap comprises one or more apertures that provide access to the biological material.

3. The test indicator of claim 1 wherein the container has liquid impermeable walls and is substantially gas non-absorptive.

4. The test indicator of claim 1 wherein the container is comprised of a material selected from the group consisting of plastic, glass, silicates and a combination thereof.

5. The test indicator of claim 1 wherein the container is cylindrical.

6. The test indicator of claim 1 wherein the cap is comprised of plastic, porous plastic, glass, sintered glass, rubber or a combination thereof.

7. The test indicator of claim 1 further comprising a sterilant-permeable insert covering the at least one opening.

8. The test indicator of claim 7 wherein the sterilant-permeable insert is selected from the group consisting of a screen, a membrane, a mesh, a bacteria permeable insert, and a combination thereof.

9. The test indicator of claim 1 wherein the cap further comprising a protruding member that prevents the biological material contained within the interior chamber from falling out of the chamber through the at least one opening.

10. The test indicator of claim 9 wherein the protruding member is selected from the group consisting of a wand, a stem, a hollow member, a solid member and a combination thereof.

11. The test indicator of claim 9 wherein the protruding member is composed of a material selected from the group consisting of plastic, rubber, glass, silicates, non-reactive metal and a combination thereof.

12. The test indicator of claim 9 wherein the protruding member is a hollow wand and the cap further comprises at least one dispensing member.

13. The test indicator of claim 12 wherein the hollow wand contains an indicator solution.

14. The test indicator of claim 1 wherein the sterilization procedure comprises steam heat, chemical sterilant, plasma, radiation, dry heat or a combination thereof.

15. The test indicator of claim 1 wherein the biological material at least one component of an interactive enzyme system.

16. The test indicator of claim 15 wherein the biological material comprises a granulation product.

17. The test indicator of claim 16 wherein the interactive enzyme system comprises a granulation product of glucose dehydrogenase and diaphorase.

18. The test indicator system of claim 1 wherein the container contains a thermal-sensitive or chemical-sensitive ink.

19. A method for determining the effectiveness of a sterilization procedure by exposing the indicator system of claim 1 to the sterilization procedure, observing the test indicator within the chamber after exposure and determining the effectiveness of the sterilization procedure.

20. A test pack for determining the effectiveness of a sterilization procedure comprising a test container having one or more openings communicating with an interior chamber that contains the test indicator of claim 1.

21. The test pack of claim 20 wherein the sterilization procedure comprises steam heat, chemical sterilant, plasma, radiation, dry heat or a combination thereof.

22. The test pack of claim 20 further comprising a sterilant-permeable cover over the one or more openings of the test container.

23. The test pack of claim 22 wherein the cover is selected from the group consisting of foam, a screen, a membrane, a mesh, a bacteria permeable insert and a combination thereof.

24. The test pack of claim 20 which can be reused upon substitution of the test indicator.

25. A method for determining the effectiveness of a sterilization procedure by exposing the test pack of claim 20 to the sterilization procedure, observing the test indicator within the chamber after exposure and determining the effectiveness of the sterilization procedure.

26. A self-contained test indicator for determining the effectiveness, of a sterilization procedure comprising:
    a container having at least one opening communicating with an interior chamber containing biological material to be used as an indicator of destruction of living organisms by the sterilization procedure;
    a cap that provides access to the biological material, wherein the cap is positioned on the at least one opening such that movement of gas between the environment surrounding the test indicator and the interior chamber occurs through the cap, and
    a vessel that contains an indicator solution.

27. The test indicator of claim 26 wherein the cap comprises one or more apertures.

28. The test indicator of claim 26 wherein the vessel is attached to the cap.

29. The test indicator of claim 26 further comprising a dispensing means that dispenses indicator solution from the vessel to the biological material.

30. A method for determining the effectiveness of a sterilization procedure comprising:
    exposing a test indicator having
        at least one opening communicating with an interior chamber containing biological material to be used as an indicator of destruction of living organisms by the sterilization procedure;
        a cap that provides access to the biological material, wherein the cap is positioned on the at least one opening such that movement of gas between the environment surrounding the test indicator and the interior chamber occurs through the cap, and
        a vessel attached to the cap that contains an indicator solution;
    exposing the test indicator to the sterilization procedure;
    dispensing the indicator solution to the biological material; and
    determining the effectiveness of the sterilization procedure.

31. The method of claim 30 wherein the cap comprises one or more apertures.

* * * * *

UNITED STATES PATENT AND TRADEMARK OFFICE
CERTIFICATE OF CORRECTION

PATENT NO. : 6,528,277 B1  
DATED : March 4, 2003  
INVENTOR(S) : Hendrricks, Judy K.

It is certified that error appears in the above-identified patent and that said Letters Patent is hereby corrected as shown below:

Column 1,  
Line 15, delete "sterilizations" and insert in place thereof -- sterilization --;

Column 10,  
Line 12, delete "a" following the word "the"

Column 11,  
Line 13, delete "place" and insert in place thereof -- placed --;

Column 12,  
Line 54, delete the word "a" following "those";

Column 13,  
Line 33, delete "made" and insert in place thereof -- may --;  
Line 36, delete "than" and insert in place thereof -- then --;

Column 15,  
Line 55, delete "12" and insert in place thereof -- ½ --;

Column 19,  
Line 36, insert the word -- comprises -- following the word "material";

Column 20,  
Line 16, delete "," preceding the word "of"

Signed and Sealed this

Twenty-fifth Day of May, 2004

JON W. DUDAS  
*Acting Director of the United States Patent and Trademark Office*